(12) United States Patent
Boutelet et al.

(10) Patent No.: US 7,045,120 B2
(45) Date of Patent: *May 16, 2006

(54) PHOTOPROTECTIVE/COSMETIC COMPOSITIONS COMPRISING SULFONIC/ HYDROPHOBIC AMPHIPHILIC POLYMERS

(75) Inventors: Karl Boutelet, Paris (FR); Didier Candau, Bievres (FR)

(73) Assignee: L'Oreal, Paris (FR)

(*) Notice: Subject to any disclaimer, the term of this patent is extended or adjusted under 35 U.S.C. 154(b) by 0 days.

This patent is subject to a terminal disclaimer.

(21) Appl. No.: 10/617,092

(22) Filed: Jul. 11, 2003

(65) Prior Publication Data

US 2004/0071641 A1  Apr. 15, 2004

Related U.S. Application Data

(63) Continuation of application No. PCT/FR02/00028, filed on Jan. 4, 2002.

(30) Foreign Application Priority Data

Jan. 11, 2001 (FR) .......................... 01 00387

(51) Int. Cl.
*A61K 7/42* (2006.01)
*A61K 7/44* (2006.01)
*A61K 31/74* (2006.01)
*A61K 7/00* (2006.01)

(52) U.S. Cl. .................. 424/59; 424/60; 424/78.02; 424/78.08; 424/400; 424/401

(58) Field of Classification Search ............... 424/59, 424/60, 78.02, 78.08, 400, 401
See application file for complete search history.

(56) References Cited

U.S. PATENT DOCUMENTS

| | | |
|---|---|---|
| 4,460,732 A | 7/1984 | Buscall et al. |
| 4,861,499 A | 8/1989 | Neff et al. |
| 5,089,578 A | 2/1992 | Valint et al. |
| 5,114,706 A | 5/1992 | Duvel |
| 5,318,995 A | 6/1994 | Mondet et al. |
| 5,464,452 A | 11/1995 | Cole et al. |
| 5,968,481 A | 10/1999 | Ascione et al. |
| 6,287,543 B1 | 9/2001 | Terren et al. |
| 6,465,402 B1 | 10/2002 | Lorant |
| 6,645,476 B1 | 11/2003 | Morschhäuser et al. |
| 2004/0109835 A1 | 6/2004 | Loffler et al. |

FOREIGN PATENT DOCUMENTS

| | | |
|---|---|---|
| EP | 0 406 042 A2 | 1/1991 |
| EP | 0 750 899 A2 | 1/1997 |
| EP | 0 815 843 A1 | 1/1998 |
| EP | 1 069 142 A1 | 1/2001 |
| EP | 1 055 406 A2 | 11/2002 |
| WO | 00/31154 A1 | 6/2000 |
| WO | 02/43689 A2 | 6/2002 |

OTHER PUBLICATIONS

Kobayashi et al., *Journal of Applied Polymer Science*, vol. 73, No. 12, Sep. 19, 1999, pp. 2447–2453, John Wiley and Sons, Inc., New York.

Patent Abstracts of Japan, vol. 1997, No. 2, Feb. 28, 1997, abstract of JP 08 252447A published Oct. 1, 1996.

*Primary Examiner*—Shelley A. Dodson
(74) *Attorney, Agent, or Firm*—Buchanan Ingersoll, P.C.

(57) ABSTRACT

Photoprotective cosmetic/dermatological compositions well suited for the UV-photoprotection of human skin and/or hair, comprise (a) particulates of at least one insoluble mineral and/or organic UV-screening agent having a particle size ranging from 5 nm to 5 μm and (b) a stabilizing amount of at least one amphiphilic polymerizate of at least one ethylenically unsaturated monomer which comprises a sulfonic group, whether in the free acid or in partially or totally neutralized state, and which amphiphilic polymerizate also comprises at least one hydrophobic moiety.

78 Claims, No Drawings

PHOTOPROTECTIVE/COSMETIC COMPOSITIONS COMPRISING SULFONIC/ HYDROPHOBIC AMPHIPHILIC POLYMERS

CROSS-REFERENCE TO PRIORITY/PCT APPLICATIONS

This application claims priority under 35 U.S.C. § 119 of FR-01/00387, filed Jan. 11, 2001, and is a continuation of PCT/FR02/00028, filed Jan. 4, 2002 and designating the United States (published in the French language on Jul. 18, 2002 as WO 02/055045 A1; the title and abstract were also published in English), both hereby expressly incorporated by reference.

CROSS-REFERENCE TO COMPANION APPLICATION

Our copending application Ser. No. 10/616,947, filed concurrently herewith and assigned to the assignee thereof.

BACKGROUND OF THE INVENTION

1. Technical Field of the Invention

The present invention relates to a cosmetic or dermatological composition comprising at least one photoprotective system capable of screening out UV rays, containing at least one insoluble mineral or organic UV-screening agent, with a particle size ranging from 5 nm to 5 µm, characterized in that it also comprises at least one amphiphilic polymer comprising at least one ethylenically unsaturated monomer containing a sulfonic group, in free form or partially or totally neutralized form, and comprising at least one hydrophobic portion.

2. Description of Background/Related/Prior Art

The invention also relates to the use of these compositions for protecting the skin and the hair against the effects of ultraviolet radiation.

It is known that light radiation with wavelengths of between 280 nm and 400 nm permit tanning of the human epidermis, and that light rays with wavelengths more particularly between 280 and 320 nm, which are known as UV-B rays, cause skin burns and erythema that may harm the development of a natural tan. For these reasons, and also for aesthetic reasons, there is a constant demand for means for controlling this natural tanning in order thus to control the color of the skin; this UV-B radiation should thus be screened out.

It is also known that UV-A rays, with wavelengths of between 320 and 400 nm, which cause tanning of the skin, are liable to induce an impairment thereof, especially in the case of sensitive skin or of skin that is continually exposed to sunlight. In particular, UV-A rays cause a loss of elasticity of the skin and the appearance of wrinkles, leading to premature aging of the skin. They promote the triggering of the erythemal reaction or amplify this reaction in certain individuals and may even be the cause of phototoxic or photoallergic reactions. Thus, for aesthetic and cosmetic reasons, for instance preserving the natural elasticity of the skin, more and more individuals wish to control the effect of UV-A rays on their skin. It is thus desirable also to screen out UV-A radiation.

Many cosmetic compositions intended for photoprotection (against UV-A and/or UV-B) of the skin have been proposed to date.

These antisun compositions are quite often in the form of an emulsion, of oil-in-water type (i.e., a cosmetically and/or dermatologically acceptable support consisting of an aqueous dispersing continuous phase and a fatty dispersed discontinuous phase) or water-in-oil type (aqueous phase dispersed in a continuous fatty phase), which contains, in varying concentrations, one or more standard lipophilic organic screening agents and/or mineral metal oxide nanopigments, capable of selectively absorbing the harmful UV radiation, these screening agents (and the amounts thereof) being selected as a function of the desired sun protection factor, the sun protection factor (SPF) mathematically expressing the ratio of the dose of UV radiation required to reach the erythema-forming threshold with the UV-screening agent to the dose of UV radiation required to reach the erythema-forming threshold without a UV-screening agent. In such emulsions, the hydrophilic screening agents are present in the aqueous phase and the lipophilic screening agents are present in the fatty phase.

Users generally prefer oil-in-water emulsions to water-in-oil emulsions, especially on account of their pleasant feel (close to water) and their presentation in the form of a milk or a non-greasy cream; however, they also more readily lose their anti-UV efficacy once they come into contact with water; the reason for this is that hydrophilic screening agents have a tendency to be lost in water, on bathing in the sea or in a swimming pool, under the shower or when practicing water sports; thus, the antisun compositions they contain, alone or combined with lipophilic screening agents, no longer provide the desired initial protection once the substrate (skin or hair) onto which they have been applied comes into contact with water.

It is possible to obtain antisun compositions with improved water resistance by using water-in-oil emulsions. The reason for this is that a hydrophilic screening agent is more water-resistant in a water-in-oil emulsion than in an oil-in-water emulsion. However, as has been mentioned above, such compositions are still not entirely satisfactory since, after they have been applied, they leave a greasy impression that users find particularly unpleasant.

Thus, there is still a need to be able to obtain antisun compositions that give the skin and/or the hair effective antisun protection, which is stable over time and water-resistant, and the cosmetic performance qualities of which are comparable to those obtained with standard oil/water emulsions.

The UV-screening agents most commonly used are organic and soluble in oils or in aqueous media; they generally contain in their structure a chromophoric group linked to a solubilizing group that is generally a fatty chain in the case of liposoluble UV-screening agents or a carboxylic or sulfonic acid group in the case of water-soluble UV-screening agents.

Micronized insoluble organic UV-screening agents with a mean particle size ranging from 10 nm to 2 µm, which have the advantage of being more effective than their soluble homologues comprising the same chromophoric group to an equivalent proportion, are known in the prior art. UV-screening agents of this type are especially described in EP-746,305 and EP-8-405,395.

Pigments or nanopigments (mean size of the primary particles: generally between 5 nm and 100 nm and preferably between 10 mu and 50 nm) of coated or uncoated metal oxides, for instance titanium oxide (amorphous or crystallized in rutile and/or anatase form), iron oxide, zinc oxide, zirconium oxide or cerium oxide nanopigments, are very frequently used in antisun formulations in combination with soluble organic UV-screening agents. Insoluble UV-screening agents of this type make it possible to increase the level of protection of the soluble organic UV-screening agents and to achieve high protection factors.

Unfortunately, it is often difficult to incorporate insoluble UV-screening agents into standard antisun formulations such as oil/water or water/oil emulsions.

SUMMARY OF THE INVENTION

It has now surprisingly and unexpectedly been determined that particular compositions containing at least one insoluble UV-screening agent and at least one amphiphilic polymer comprising at least one ethylenically unsaturated monomer containing a sulfonic group, in free form or partially or totally neutralized form and comprising at least one hydrophobic portion, not only make it possible to obtain stable antisun compositions whose cosmetic performance qualities are comparable with those generally obtained with a standard antisun composition in oil/water emulsion form, but also show improved water resistance.

These discoveries form the basis of the present invention.

One subject of the present invention is a cosmetic or dermatological composition comprising at least one mineral or organic insoluble UV-screening agent, with a mean particle size ranging from 5 nano-metres to 5 μm, characterized in that it also comprises at least one amphiphilic polymer comprising at least one ethylenically unsaturated monomer containing a sulfonic group, in free form or partially or totally neutralized form, and comprising at least one hydrophobic portion or moiety.

For the purposes of the present invention, the expression "insoluble UV-screening agent" means any organic or mineral UV-screening agent with a water solubility of less than 0.1% by weight and a solubility of less than 1% by weight in most organic solvents, for instance liquid paraffin, fatty alkyl benzoates and fatty acid triglycerides, for example Miglyol® 812 sold by Dynamit Nobel. This solubility, defined at 70° C. as the amount of product in solution in the solvent at equilibrium with an excess of solid in suspension, may be readily evaluated in the laboratory.

A subject of the present invention is also the use of the emulsion for manufacturing cosmetic compositions for protecting the skin and/or the hair against ultraviolet radiation and in particular sunlight.

Other characteristics, aspects and advantages of the present invention will become apparent on reading the detailed description that follows.

DETAILED DESCRIPTION OF BEST MODE AND SPECIFIC/PREFERRED EMBODIMENTS OF THE INVENTION

The polymers in accordance with the invention are amphiphilic polymers comprising at least one ethylenically unsaturated monomer containing a sulfonic group, in free form or partially or totally neutralized form, and comprising at least one hydrophobic portion.

The expression "amphiphilic polymer" means any polymer comprising both a hydrophilic portion and a hydrophobic portion and especially a fatty chain.

The hydrophobic portion present in the polymers of the invention preferably contains from 6 to 50 carbon atoms, more preferably from 6 to 22 carbon atoms, even more preferably from 6 to 18 carbon atoms and more particularly from 12 to 18 carbon atoms.

Preferably, the polymers in accordance with the invention are partially or totally neutralized with a mineral base (sodium hydroxide, potassium hydroxide or aqueous ammonia) or an organic base such as mono-, di- or triethanolamine, an aminomethylpropanediol, N-methylglucamine, basic amino acids, for instance arginine and lysine, and mixtures of these compounds.

The amphiphilic polymers in accordance with the invention generally have a number-average molecular weight ranging from 1,000 to 20,000,000 g/mol, preferably ranging from 20,000 to 5,000,000 and even more preferably from 100,000 to 1,500,000 g/mol.

The amphiphilic polymers according to the invention may or may not be crosslinked. Crosslinked amphiphilic polymers are preferably chosen. When they are crosslinked, the crosslinking agents may be chosen from polyolefinically unsaturated compounds commonly used for the crosslinking of polymers obtained by free-radical polymerization.

Mention may be made, for example, of divinylbenzene, diallyl ether, dipropylene glycol diallyl ether, polyglycol diallyl ethers, triethylene glycol divinyl ether, hydroquinone diallyl ether, ethylene glycol di(meth)acrylate or tetraethylene glycol di(meth)-acrylate, trimethylolpropane triacrylate, methylenebis-acrylamide, methylenebismethacrylamide, triallylamine, triallyl cyanurate, diallyl maleate, tetraallylethylenediamine, tetraallyloxyethane, trimethylol-propane diallyl ether, allyl (meth)acrylate, allylic ethers of alcohols of the sugar series, or other allyl or vinyl ethers of polyfunctional alcohols, and also allylic esters of phosphoric and/or vinylphosphonic acid derivatives, or mixtures of these compounds.

Methylenebisacrylamide, allyl methacrylate or trimethylolpropane triacrylate (TMPTA) will be used more particularly. The degree of crosslinking will generally range from 0.01 mol % to 10 mol % and more particularly from 0.2 mol % to 2 mol % relative to the polymer.

The ethylenically unsaturated monomers containing a sulfonic group are chosen especially from vinylsulfonic acid, styrenesulfonic acid, (meth)acrylamido($C_1$–$C_{22}$) alkylsulfonic acids, and N-($C_1$–$C_{22}$)alkyl(meth)acrylamido ($C_1$–$C_{22}$)alkylsulfonic acids, for instance undecylacrylamidomethanesulfonic acid, and also partially or totally neutralized forms thereof.

(Meth)acrylamido($C_1$–$C_{22}$)alkylsulfonic acids such as, for example, acrylamidomethanesulfonic acid, acrylamidoethanesulfonic acid, acrylamidopropane-sulfonic acid, 2-acrylamido-2-methylpropanesulfonic acid, methacrylamido-2-methylpropanesulfonic acid, 2-acrylamido-n-butanesulfonic acid, 2-acrylamido-2,4,4-trimethylpentanesulfonic acid, 2-methacrylamidododecylsulfonic acid or 2-acrylamido-2,6-dimethyl-3-heptanesulfonic acid, and also partially or totally neutralized forms thereof, will more preferably be used.

2-Acrylamido-2-methylpropanesulfonic acid (AMPS), and also partially or totally neutralized forms thereof, will more particularly be used.

The amphiphilic polymers in accordance with the invention may be chosen especially from random amphiphilic AMPS polymers modified by reaction with a $C_6$–$C_{22}$ n-monoalkylamine or di-n-alkylamine, and such as those described in WO 00/31154 (forming an integral part of the content of the description). These polymers may also contain other ethylenically unsaturated hydrophilic monomers chosen, for example, from (meth)acrylic acids, β-substituted alkyl derivatives thereof or esters thereof obtained with monoalcohols or mono- or polyalkylene glycols, (meth) acrylamides, vinylpyrrolidone, maleic anhydride, itaconic acid or maleic acid, or mixtures of these compounds.

The preferred polymers of the invention are chosen from amphiphilic copolymers of AMPS and of at least one ethylenically unsaturated hydrophobic monomer comprising at least one hydrophobic portion containing from 6 to 50 carbon atoms, more preferably from 6 to 22 carbon atoms, even more preferably from 6 to 18 carbon atoms and more particularly 12 to 18 carbon atoms. These same copolymers may also contain one or more ethylenically unsaturated monomers not comprising a fatty chain, such as (meth) acrylic acids, β-substituted alkyl derivatives thereof or esters thereof obtained with monoalcohols or mono- or polyalkylene glycols, (meth)acrylamides, vinylpyrrolidone, maleic anhydride, itaconic acid or maleic acid, or mixtures of these compounds.

These copolymers are described especially in EP-A-750 899, U.S. Pat. No. 5,089,578 and in the following publications from Yotaro Morishima:

"Self-assembling amphiphilic polyelectrolytes and their nanostructures—Chinese Journal of Polymer Science Vol. 18, No. 40, (2000), 323–336";

"Micelle formation of random copolymers of sodium 2-(acrylamido)-2-methylpropanesulfonate and a nonionic surfactant macromonomer in water as studied by fluorescence and dynamic light scattering—Macromolecules 2000, Vol. 33, No. —3694–3704";

"Solution properties of micelle networks formed by nonionic moieties covalently bound to a polyelectrolyte: salt effects on rheological behaviour—Langmuir, 2000, Vol. 16, No. 12, 5324–5332";

"Stimuli responsive amphiphilic copolymers of sodium 2-(acrylamido)-2-methylpropanesulfonate and associative macromonomers—Polym. Preprint, Div. Polym. Chem. 1999, 40(2), 220–221".

The ethylenically unsaturated hydrophobic monomers of these particular copolymers are preferably chosen from the acrylates or acrylamides of formula (I) below:

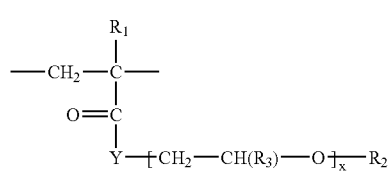

(I)

in which $R_1$ and $R_3$, which may be identical or different, denote a hydrogen atom or a linear or branched $C_1$–$C_6$ alkyl radical (preferably methyl); Y is O or NH; $R_2$ is a hydrophobic hydrocarbon-based radical containing at least from 6 to 50 carbon atoms, more preferably from 6 to 22 carbon atoms, even more preferably from 6 to 18 carbon atoms and more particularly from 12 to 18 carbon atoms; x is a number of moles of alkylene oxide and ranges from 0 to 100.

The radical $R_2$ is preferably chosen from linear $C_6$–$C_{18}$ alkyl radicals (for example n-hexyl, n-octyl, n-decyl, n-hexadecyl and n-dodecyl) and branched or cyclic $C_6$–$C_{18}$ alkyl radicals (for example cyclododecane ($C_{12}$) or adamantane ($C_{10}$)); $C_6$–$C_{18}$ alkyl-perfluoro radicals (for example the group of formula —$(CH_2)_2$—$(CF_2)9$-$CF_3$); the cholesteryl radical ($C_{27}$) or a cholesterol ester residue, for instance the cholesteryl oxyhexanoate group; aromatic polycyclic groups, for instance naphthalene or pyrene. Among these radicals, the ones that are more particularly preferred are linear alkyl radicals and more particularly the n-dodecyl radical.

According to one particularly preferred form of the invention, the monomer of formula (I) comprises at least one alkylene oxide unit ($x \geq 1$) and preferably a polyoxyalkylenated chain. The polyoxyalkylenated chain preferably consists of ethylene oxide units and/or of propylene oxide units and even more particularly consists of ethylene oxide units. The number of oxyalkylene units generally ranges from 3 to 100, more preferably from 3 to 50 and even more preferably from 7 to 25.

Among these polymers, mention may be made of:

crosslinked or non-crosslinked, neutralized or non-neutralized copolymers comprising from 15% to 60% by weight of AMPS units and from 40% to 85% by weight of ($C_8$–$C_{16}$)alkyl(meth)acrylamide units or of ($C_8$–$C_{16}$) alkyl (meth)acrylate units, relative to the polymer, such as those described in EP-A-750 899;

terpolymers comprising from 10 mol % to 90 mol % of acrylamide units, from 0.1 mol % to 10 mol % of AMPS units and from 5 mol % to 80 mol % of n-($C_6$–$C_{18}$)alkyl-acrylamide units, such as those described in U.S. Pat. No. 5,089,578.

Mention may also be made of copolymers of totally neutralized AMPS and of dodecyl methacrylate, and also crosslinked and non-crosslinked copolymers of AMPS and of n-dodecylmethacrylamide, such as those described in the Morishima articles mentioned above.

Mention will be made more particularly of the copolymers of 2-acrylamido-2-methylpropane-sulfonic acid (AMPS) units of formula (II) below:

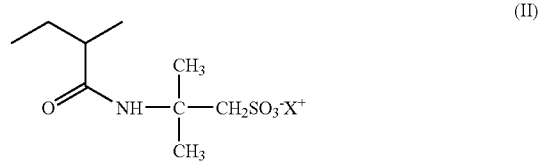

(II)

in which $X^+$ is a proton, an alkali metal cation, an alkaline-earth metal cation or the ammonium ion, and of units of formula (III) below:

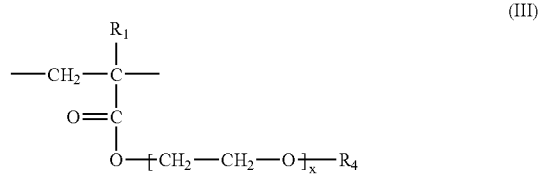

(III)

in which x is an integer ranging from 3 to 100, preferably from 5 to 80 and more preferably from 7 to 25; $R_1$ has the same meaning as that given above in formula (I) and $R_4$ is a linear or branched $C_6$–$C_{22}$ and more preferably $C_{10}$–$C_{22}$ alkyl.

The polymers that are particularly preferred are those for which x=25, $R_1$ is methyl and $R_4$ represents n-dodecyl; they are described in the Morishima articles mentioned above. The polymers for which $X^+$ is sodium or ammonium are more particularly preferred.

The preferred amphiphilic polymers in accordance with the invention may be obtained according to the standard free-radical polymerization processes in the presence of one or more initiators such as, for example, azobisisobutyronitrile (AIBN), azobisdimethyl-valeronitrile, ABAH (2,2-azobis[2-amidinopropane] hydrochloride), organic peroxides such as dilauryl peroxide, benzoyl peroxide, tert-butyl hydroperoxide, etc., mineral peroxide compounds such as potassium persulfate or ammonium persulfate, or $H_2O_2$ optionally in the presence of reducing agents.

The amphiphilic polymers are obtained especially by free-radical polymerization in tert-butanol medium in which they precipitate.

Using precipitation polymerization in tert-butanol, it is possible to obtain a size distribution of the polymer particles that is particularly favorable for its uses.

The size distribution of the polymer particles may be determined, for example, by laser diffraction or image analysis.

An advantageous distribution for this type of polymer, determined by image analysis, is as follows: 60.2% less than 423 microns, 52.0% less than 212 microns, 26.6% less than 106 microns, 2.6% less than 45 microns and 26.6% greater than 850 microns.

The reaction may be performed at a temperature of between 0° C. and 150° C., preferably between 10° C. and 100° C., either at atmospheric pressure or under reduced pressure. It may also be performed under inert atmosphere, and preferably under nitrogen.

According to this process 2-acrylamido-2-methylpropane-sulfonic acid (AMPS) or a sodium or ammonium salt thereof was especially polymerized with a (meth) acrylic acid ester and a $C_{10}$–$C_{18}$ alcohol oxyethylenated with 8 mol of ethylene oxide (Genapol® C-080 from the company Hoechst/Clariant), a $C_{11}$ oxo alcohol oxyethylenated with 8 mol of ethylene oxide (Genapol® UD-080 from the company Hoechst/Clariant), a $C_{11}$ oxo alcohol oxyethylenated with 7 mol of ethylene oxide (Genapol® UD-070 from the company Hoechst/Clariant), a $C_{12}$–$C_{14}$ alcohol oxyethylenated with 7 mol of ethylene oxide (Genapol® LA-070 from the company Hoechst/Clariant), a $C_{12}$–$C_{14}$ alcohol oxyethylenated with 9 mol of ethylene oxide (Genapol® LA-090 from the company Hoechst/Clariant), a $C_{12}$–$C_{14}$ alcohol oxyethylenated with 11 mol of ethylene oxide (Genapol® LA-110 from the company Hoechst/Clariant), a $C_{16}$–$C_{18}$ alcohol oxyethylenated with 8 mol of ethylene oxide (Genapol® T-080 from the company Hoechst/Clariant), a $C_{16}$–$C_{18}$ alcohol oxyethylenated with 15 mol of ethylene oxide (Genapol® T-150 from the company Hoechst/Clariant), a $C_{16}$–$C_{18}$ alcohol oxyethylenated with 11 mol of ethylene oxide (Genapol® T-110 from the company Hoechst/Clariant), a $C_{16}$–$C_{18}$ alcohol oxyethylenated with 20 mol of ethylene oxide (Genapol® T-200 from the company Hoechst/Clariant), a $C_{16}$–$C_{18}$ alcohol oxyethylenated with 25 mol of ethylene oxide (Genapole T-250 from the company Hoechst/Clariant), a $C_{18}$–$C_{22}$ alcohol oxyethylenated with 25 mol of ethylene oxide and/or a $C_{16}$–$C_{18}$ iso alcohol oxyethylenated with 25 mol of ethylene oxide.

The molar % concentration of the units of formula (II) and of the units of formula (III) in the polymers according to the invention will vary as a function of the desired cosmetic use and of the desired rheological properties of the formulation. It may range between 0.1 mol% and 99.9 mol %.

Preferably, for the most hydrophobic polymers, the molar proportion of units of formula (I) or (III) ranges from 50.1% to 99.9%, more particularly from 70% to 95% and even more particularly from 80% to 90%. Preferably, for the sparingly hydrophobic polymers, the molar proportion of units of formula (I) or (III) ranges from 0.1% to 50%, more particularly from 5% to 25% and even more particularly from 10% to 20%. The monomer distribution in the polymers of the invention may be, for example, alternating, block (including multiblock) or random.

According to the invention, it is preferable for the polymers to contain heat-sensitive pendant chains and for the aqueous solution thereof to have a viscosity that, beyond a certain threshold temperature, increases or remains virtually constant as the temperature increases.

Even more particularly, the preferred polymers are those whose aqueous solution has a viscosity that is low below a first threshold temperature and that, above this first threshold temperature, increases to a maximum as the temperature increases, and that, above a second threshold temperature, decreases again as the temperature increases. From this perspective, it is preferable for the viscosity of the polymer solutions below the first threshold temperature to be from 5% to 50%, in particular from 10% to 30% of the maximum viscosity at the second threshold temperature.

These polymers preferably lead in water to a phenomenon of demixing by heating, reflected by curves showing, as a function of the temperature and the concentration, a minimum known as the LCST (Lower Critical Solution Temperature).

The viscosities (measured at 25° C. using a Brookfield viscometer, needle No. 7) of the aqueous 1% solutions preferably range from 20,000 mPa.s to 100,000 mPa.s and more particularly from 60,000 mPa.s to 70,000 mPa.s.

The amphiphilic polymers in accordance with the invention are present in the compositions in concentrations ranging from 0.01% to 30% by weight, more preferably from 0.1% to 10%, even more preferably from 0.1% to 5% by weight and even more particularly from 0.5% to 2% by weight.

The insoluble UV-screening agents according to the invention have a mean particle size which ranges from 5 nanometres (nm) to 5 μm, more preferably from 10 nm to 2 μm and more particularly from 20 nm to 2 μm. The insoluble UV-screening agents in accordance with the invention are generally pigments or more particularly nanopigments (mean size of the primary particles: generally between 5 nm and 100 nm and preferably between 10 nm and 50 nm) of coated or uncoated metal oxides, for instance titanium oxide (amorphous or crystallized in rutile and/or anatase form), iron oxide, zinc oxide, zirconium oxide or cerium oxide nanopigments, which are all UV-photo-protective agents that are well known per se. Alumina and/or aluminum stearate are also standard coating agents. Such coated or uncoated metal oxide nanopigments are described in particular in EP-A-0-518,772 and EP-A-0-518,773.

The insoluble organic screening agents according to the invention may be placed in the desired particulate form by any suitable means such as, especially, dry-grinding or grinding in solvent medium, screening, atomization, micronization or spraying. The insoluble organic screening agents according to the invention in micronized form may be obtained in particular by a process of grinding an insoluble organic UV-screening agent in the form of coarse particles in the presence of a suitable surfactant for improving the dispersion of the particles thus obtained in the cosmetic formulations.

An example of a process for micronizing insoluble organic screening agents is described in GB-A-2-303,549 and EP-A-893, 119, which form an integral part of the description. The grinding machine used in these documents may be a jet mill, a ball mill, a vibration mill or a hammer mill, and preferably a mill at high stirring speed or an impact mill and more particularly a rotating ball mill, a vibrating mill, a tube mill or a rod mill.

According to this particular process, alkyl-polyglucosides of structure $C_nH_{2n+1}O(C_6H_{10}O_5)_xH$ in which n is an integer from 8 to 16 and x is the average degree of polymerization of the $(C_6H_{10}O_5)$ unit and ranges from 1.4 to 1.6, are used as surfactants for grinding the said screening agents. They may be chosen from $C_1$–$C_{12}$ esters of a compound of structure $C_nH_{2n+1}O(C_6H_{10}O_5)_xH$ and more specifically an ester obtained by reacting a $C_1$–$C_{12}$ carboxylic acid such as formic acid, acetic acid, propionic acid, butyric acid, sulfosuccinic acid, citric acid or tartaric acid with one or more free OH functions on the glucoside unit $(C_6H_{10}O_5)$. The said surfactants are generally used at a concentration ranging from 1% to 50% by weight and more preferably from 5% to 40% by weight relative to the insoluble screening agent in its micronized form.

The insoluble organic UV-screening agents in accordance with the invention may be chosen especially from organic UV-screening agents of the oxanilide type, of the triazine type, of the triazole type, of the vinyl amide type, of the cinnamide type, of the type comprising one or more benzazole and/or benzofuran or benzothiophene groups, or of the indole type.

In the sense that it is used in the present invention, the term "benzazole" covers both benzo-thiazoles, benzoxazoles and benzimidazoles.

Among the UV-screening agents of the oxanilide type in accordance with the invention, mention may be made of those corresponding to the structure:

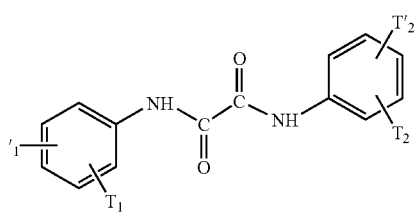

(1)

in which $T_1$, $T'_1$, $T_2$ and $T'_2$, which may be identical or different, denote a $C_1$–$C_8$ alkyl radical or a $C_1$–$C_8$ alkoxy radical. These compounds are described in WO 95/22959.

Examples that may be mentioned include commercial products Tinuvin 315 and Tinuvin 312 sold by Ciba-Geigy and having the respective structures:

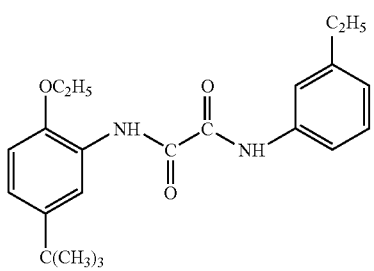

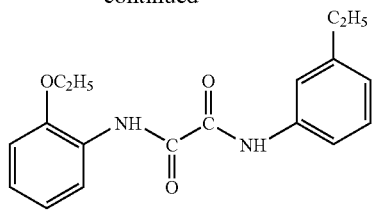

Among the UV-screening agents of the triazine type in accordance with the invention, mention may also be made of insoluble s-triazine derivatives bearing benzalmalonate and/or phenylcyanoacrylate groups, such as those described in EP-A-0-790,243 (which forms an integral part of the content of the description).

Among these insoluble UV-screening agents of the triazine type, mention will be made more particularly of the following compounds:
2,4,6-tris(diethyl 4'-aminobenzalmalonate)-s-triazine,
2,4,6-tris(diisopropyl 4'-aminobenzalmalonate)-s-triazine,
2,4,6-tris(dimethyl 4'-aminobenzalmalonate)-s-triazine,
2,4,6-tris(ethyl α-cyano-4-aminocinnamate)-s-triazine.

Among the insoluble UV-screening agents of the triazine type in accordance with the invention, mention may also be made of those corresponding to formula (2) below:

$$\begin{array}{c}\text{(2)}\\ \text{triazine structure with } T_3, T_4, T_5\end{array}$$

in which $T_3$, $T_4$ and $T_5$, independently, are phenyl, phenoxy or pyrrolo, in which the phenyl, phenoxy and pyrrolo are optionally substituted with one, two or three substituents chosen from OH, $C_1$–$C_{18}$ alkyl or alkoxy, $C_1$–$C_{18}$ carboxyalkyl, $C_5$–$C_8$ cycloalkyl, a methylidenecamphor group or a group $-(CH=CH)_n(CO)-OT_6$, with $T_6$ being either $C_1$–$C_{18}$ alkyl or cinnamyl.

These compounds are described in WO 97/03642, GB-2-286,774, EP-743 309, WO 98/22447 and GB-2-319,523 (which form an integral part of the content of the description).

Among the UV-screening agents of the triazine type in accordance with the invention, mention may also be made of insoluble s-triazine derivatives bearing benzotriazole and/or benzothiazole groups, such as those described in WO 98/25922 (which forms an integral part of the content of the description).

Among these compounds, mention may be made more particularly of:
2,4,6-tris[(3'-benzotriazol-2-yl-2'-hydroxy-5'-methyl) phenylamino]-s-triazine,
2,4,6-tris[(3'-benzotriazol-2-yl-2'-hydroxy-5'-tert-octyl) phenylamino]-s-triazine.

Among the insoluble organic UV-screening agents of the triazole type in accordance with the invention, mention may be made of those of formula (3) below as described in WO 95/22959 (which forms an integral part of the content of the description):

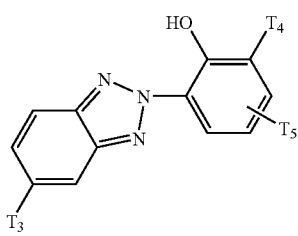

(3)

in which $T_3$ is a hydrogen atom or a $C_1$–$C_{18}$ alkyl radical; $T_4$ and $T_5$, which may be identical or different, denote a $C_1$–$C_{18}$ alkyl radical optionally substituted with a phenyl.

Examples of compounds of formula (3) that may be mentioned include the commercial products Tinuvin 328, 320, 234 and 350 from the company Ciba-Geigy, having the following structures:

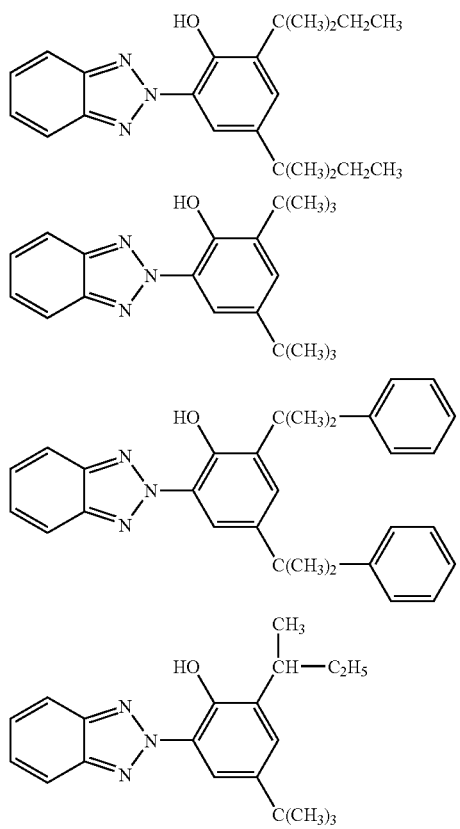

Among the insoluble organic UV-screening agents of the triazole type in accordance with the invention, mention may be made of the compounds as described in U.S. Pat. Nos. 5,687,521, 5,687,521, 5,373,037 and 5,362,881 and in particular [2,4'-dihydroxy-3-(2H-benzotriazol-2-yl)-5-(1,1,3,3-tetramethylbutyl)-2'-n-octoxy-5'-benzoyl]-diphenylmethane sold under the name Mixxim PB30 by Fairmount Chemical, having the structure:

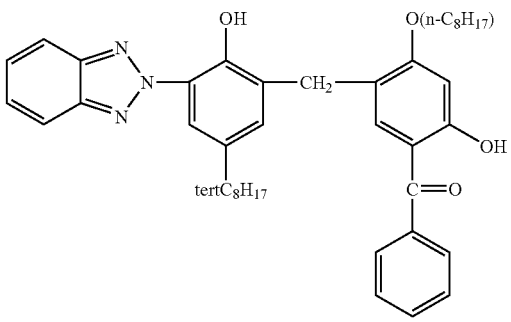

Among the insoluble organic UV-screening agents of the benzotriazole type in accordance with the invention, mention may be made of the methylenebis-(hydroxyphenylbenzotriazole) derivatives having the following structure:

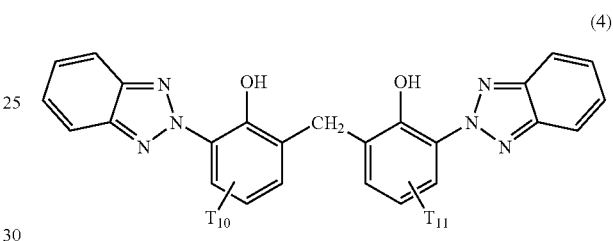

(4)

in which the radicals $T_{10}$ and $T_{11}$, which may be identical or different, denote a $C_1$–$C_{18}$ alkyl radical that may be substituted with one or more radicals chosen from $C_1$–$C_4$ alkyl, $C_5$–$C_{12}$ cycloalkyl and an aryl residue. These compounds are known per se and are described in U.S. Pat. Nos. 5,237,071, 5,166,355, GB-A-2,303,549, DE-197,26,184 and EP-A-893,119 (which form an integral part of the description).

In formula (4) defined above: the $C_1$–$C_{18}$ alkyl groups may be linear or branched and are, for example, methyl, ethyl, n-propyl, isopropyl, n-butyl, isobutyl, tert-butyl, tert-octyl, n-amyl, n-hexyl, n-heptyl, n-octyl, isooctyl, n-nonyl, n-decyl, n-undecyl, n-dodecyl, tetradecyl, hexadecyl or octadecyl; the $C_5$–$C_{12}$ cycloalkyl groups are, for example, cyclopentyl, cyclohexyl or cyclooctyl; the aryl groups are, for example, phenyl or benzyl.

Among the compounds of formula (4) that are more particularly preferred are those having the following structures:

compound (a)

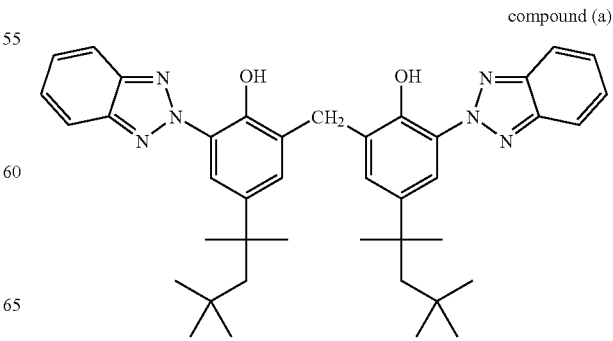

compound (b)

[Structure: bis(benzotriazolyl-tert-butylphenol) methylene compound]

compound (c)

[Structure: 2,2'-methylenebis[6-(2H-benzotriazol-2-yl)-4-(methyl)-phenol]]

Compound (a), whose nomenclature is 2,2'-methylenebis[6-(2H-benzotriazol-2-yl)-4-(1,1,3,3-tetramethylbutyl)phenol], is sold in solid form under the name Mixxim BB/100 by Fairmount Chemical, and in micronized form under the name Tinosorb M by Ciba Specialty Chemicals.

Compound (c), the nomenclature of which is 2,2'-methylenebis[6-(2H-benzotriazol-2-yl)-4-(methyl)-phenol], is sold in solid form under the name Mixxim BB/200 by Fairmount Chemical.

Among the insoluble organic screening agents of the vinyl amide type that may be mentioned, for example, are the compounds having the formula below, which are described in WO 95/22959 (which forms an integral part of the content of the description):

$$T_{12}\text{-}(Y)r\text{-}C(=O)\text{---}C(T_{13})=C(T_{14})\text{-}N(T_{15})(T_{16}) \quad (5)$$

in which $T_{12}$ is a $C_1$–$C_{18}$ and preferably $C_1$–$C_5$ alkyl radical or a phenyl group optionally substituted with one, two or three radicals chosen from OH, $C_1$–$C_{18}$ alkyl and $C_1$–$C_8$ alkoxy, or a group —C(=O)—$OT_{17}$ in which $T_{17}$ is a $C_1$–$C_{18}$ alkyl; $T_{13}$, $T_{14}$, $T_{15}$ and $T_{16}$, which may be identical or different, denote a $C_1$–$C_{18}$ and preferably $C_1$–$C_5$ alkyl radical or a hydrogen atom; Y is N or O and r is 0 or 1.

Among these compounds, mention will be made more particularly of:
4-octylamino-3-penten-2-one;
ethyl 3-octylamino-2-butenoate;
3-octylamino-1-phenyl-2-buten-1-one,
3-dodecylamino-1-phenyl-2-buten-1-one.

Among the insoluble organic screening agents of the cinnamamide type in accordance with the invention, mention may also be made of the compounds as described in WO 95/22959 (which forms an integral part of the content of the description) and corresponding to the following structure:

$$T_{18}O\text{---}\phantom{x}\text{---}CH=CH\text{---}C(=O)\text{---}N\begin{pmatrix}T_{19}\\T_{20}\end{pmatrix} \quad (6)$$

in which $OT_{18}$ is a hydroxyl or $C_1$–$C_4$ alkoxy, preferably methoxy or ethoxy, radical; $T_{19}$ is hydrogen or $C_1$–$C_4$ alkyl, preferably methyl or ethyl; $T_{20}$ is a group —(CONH)s-phenyl in which s is 0 or 1 and the phenyl group may be substituted with one, two or three groups chosen from OH, $C_1$–$C_{18}$ alkyl and $C_1$–$C_8$ alkoxy, or a group —C(=O)—$OT_{21}$ in which $T_{21}$ is a $C_1$–$C_{18}$ alkyl and $T_{21}$ is more preferably a phenyl, 4-methoxyphenyl or phenylaminocarbonyl group.

Mention may also be made of cinnamamide dimers such as those described in U.S. Pat. No. 5,888,481, for instance the compound of structure:

[Structure: cinnamamide dimer compound]

Among the insoluble organic screening agents of the benzazole type, mention may be made of those corresponding to one of the following formulae:

$$(A)_p\!\left[\!\begin{array}{c}\text{Z}\\ \text{X}\end{array}\!\text{---}(R_1)_m\right]_n \quad (7)$$

$$(R_1)_m\text{---}\!\left[\!N\!\right]_q\!\text{---}\!\begin{array}{c}\text{Z}\\ \text{X}\end{array}\!\text{---}\!\begin{array}{c}\text{Z}\\ \text{X}\end{array}\!\text{---}\!\left[\!N\!\right]_q\!\text{---}\!(R_1)_m \quad (8)$$

$$(R_1)_m\text{---}\!\begin{array}{c}\text{Z}\\ \text{X}\end{array}\!\text{---}\!\begin{array}{c}\text{Z}\\ \text{X}\end{array}\!\text{---}(R_1)_m \quad (9)$$

in which each of the symbols X independently represents an oxygen or sulfur atom or a group $NR_2$, each of the symbols Z independently represents a nitrogen atom or a CH group, each of the symbols $R_1$ independently represents an OH group, a halogen atom, a linear or branched $C_1$–$C_8$ alkyl group optionally containing a silicon atom, or a linear or branched $C_1$–$C_8$ alkoxy group, each of the numbers m is independently 0, 1 or 2, n represents an integer between 1 and 4 inclusive, p is equal to 0 or 1, each of the numbers q is independently equal to 0 or 1, each of the symbols $R_2$ independently represents a hydrogen atom, a benzyl group or a linear or branched $C_1$–$C_8$ alkyl group optionally containing a silicon atom, A represents a radical of valency n chosen from those of formulae:

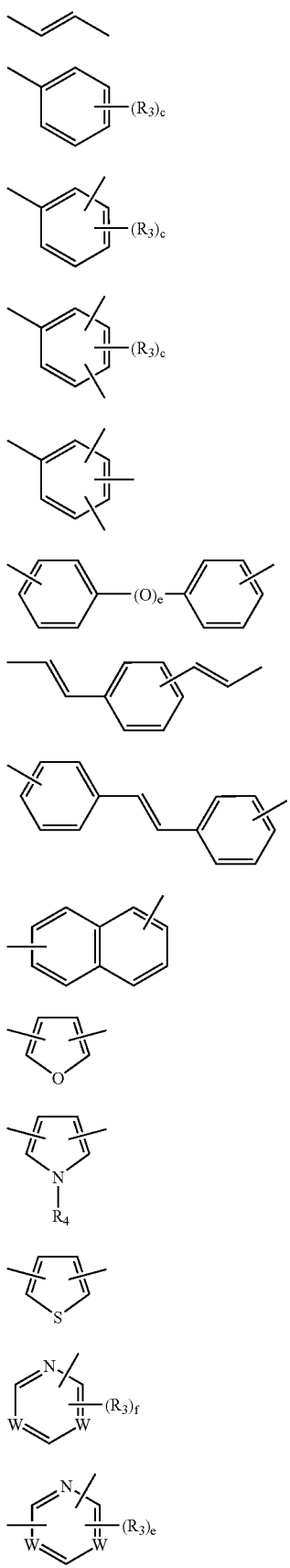

$$\begin{array}{c}\text{(o)}\\ \includegraphics\end{array}$$

in which each of the symbols $R_3$ independently represents a halogen atom or a linear or branched $C_1$–$C_4$ alkyl or alkoxy group, or hydroxyl, $R_4$ represents a hydrogen atom or a linear or branched $C_1$–$C_4$ alkyl group, c=0–4, d=0–3, e=0 or 1 and f=0–2.

These compounds are especially described in DE-676,103 and CH-350,763, U.S. Pat. Nos. 5,501,850, 5,961,960, EP-0-669,323, U.S. Pat. Nos. 5,518,713, 2,463,264, the article from *J. Am. Chem. Soc.*, 79, 5706–5708, 1957, the article from *J. Am. Chem. Soc.*, 82, 609–611, 1960, EP-0-921,126 and EP-712,855.

As examples of preferred compounds of formula (7) of the 2-arylbenzazole family, mention may be made of 2-benzoxazol-2-yl-4-methylphenol, 2-(1H-benzimidazol-2-yl)-4-methoxyphenol or 2-benzothiazol-2-ylphenol, these compounds possibly being prepared, for example, according to the processes described in CH-350,763.

As examples of preferred compounds of formula (7) of the benzimidazolylbenzazole family, mention will be made of 2,2'-bis(benzimidazole), 5,5',6,6'-tetramethyl-2,2'-bis (benzimidazole), 5,5'-di-methyl-2,2'-bis(benzimidazole), 6-methoxy-2,2'-bis(benz-imidazole), 2-(1H-benzimidazol-2-yl)benzothiazole), 2-(1H-benzimidazol-2-yl)benzoxazole and N,N'-dimethyl-2,2'-bis(benximidazole), these compounds possibly being prepared according to the procedures described in U.S. Pat. Nos. 5,961,960 and 2,463,264.

As examples of preferred compounds of formula (7) of the phenylenebenzazole family, mention will be made of 1,4-phenylenebis(2-benzoxazolyl), 1,4-phenylenebis(2-benzimidazolyl), 1,3-phenylenebis(2-benzoxazolyl), 1,2-phenylenebis(2-benzoxazolyl), 1,2-phenylenbis (benzimidazolyl), 1,4-phenylenebis(N-2-ethylhexyl-2-benzimidazolyl) and 1,4-phenylenebis(N-trimethylsilylmethyl-2-benzimidazolyl), these compounds possibly being prepared according to the procedures described in U.S. Pat. No. 2,463,264 and in the publications *J. Am. Chem. Soc.*, 82, 609 (1960) and *J. Am. Chem. Soc.*, 79, 5706–5708 (1957).

As examples of preferred compounds of formula (7) of the benzofurylbenzoxazole family, mention will be made of 2-(2-benzofuryl)benzoxazole, 2-(benzofuryl)-5-methylbenzoxazole and 2-(3-methyl-2-benzofuryl) benzoxazole, these compounds possibly being prepared according to the procedures described in U.S. Pat. No. 5,518,713.

Preferred compounds of formula (8) that may be mentioned, for example, include 2,6-diphenyl-1,7-dihydrobenzo[1,2-d;4,5-d']diimidazole, corresponding to the formula:

or 2,6-distyryl-1,7-dihydrobenzo[1,2-d;4,5-d']diimidazole or alternatively 2,6-di(p-tert-butylstyryl)-1,7-dihydro-benzo [1,2-d;4,5-d']diimidazole, which may be prepared according to EP-0-669,323.

A preferred compound of formula (9) that may be mentioned is 5,5'-bis[(2-phenyl)benzimidazole] of formula:

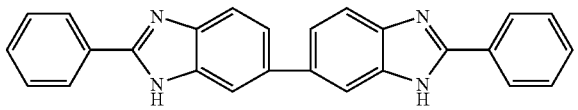

the preparation of which is described in *J. Chim. Phys.*, 64, 1602 (1967).

Among these insoluble organic compounds for screening out UV radiation, the ones most particularly preferred are 2-(1H-benzimidazol-2-yl)benzoxazole, 6-methoxy-2,2'-bis(benzimidazole), 2-(1H-benzimidazol-2-yl)benzothiazole, 1,4-phenylenebis(2-benzoxazolyl), 1,4-phenylenebis(2-benzimidazlyl), 1,3-phenylenebis-(2-benzoxazolyl), 1,2-phenylenebis(2-benzoxazolyl), 1,2-phenylenebis(2-benzimidazolyl) and 1,4-phenylene-bis(N-trimethylsilylmethyl-2-benzimidazolyl).

Another particular family of insoluble organic screening agents in accordance with the invention is the multivalent metal salts (for example $Ca^{2+}$, $Zn^{2+}$, $Mg^{2+}$, $Ba^{2+}$, $Al^{3+}$ or $Zr^{4+}$) of sulfonic or carboxylic organic screening agents such as the multivalent metal salts of sulfonated benzylidene-camphor derivatives, such as those described in FR-A-2-639,347; multivalent metal salts of sulfonated benzimidazole derivatives, such as those described in EP-A-893,119; multivalent metal salts of cinnamic acid derivatives, such as those described in JP-87-166,517.

Mention may also be made of complexes of metals or of ammonium or of substituted ammonium of UV-A and/or UV-B organic screening agents, as described in WO 93/10753, WO 93/11095 and WO 95/05150.

The insoluble UV-screening agent(s) of the invention is(are) present in a total concentration of between 0.1% and 25% by weight approximately and preferably between 0.2% and 20% by weight approximately, relative to the total weight of the composition.

The compositions in accordance with the invention may also contain UV-A-active and/or UV-B-active soluble organic UV-screening agents. They are chosen especially from anthranilates; cinnamic derivatives; dibenzoylmethane derivatives; salicylic derivatives; camphor derivatives; triazine derivatives such as those described in U.S. Pat. No. 4,367,390, EP-863,145, EP-517,104, EP-570,838, EP-796,851, EP-775,698, EP-878,469 and EP-933,376; benzophenone derivatives; β,β'-diphenylacrylate derivatives; benzotriazole derivatives; benzimidazole derivatives; imidazolines; bis-benzazolyl derivatives as described in EP-669,323 and U.S. Pat. No. 2,463,264; p-aminobenzoic acid (PABA) derivatives; screening polymers and screening silicones such as those described especially in WO 93/04665; dimers derived from α-alkylstyrene, such as those described in DE-198.55.649; 4,4-diarylbutadienes such as those described in EP-0-967,200 and DE-197,55,649; and mixtures thereof.

As examples of additional UV-A-active and/or UV-B-active organic screening agents, mention may be made of the following, denoted herein below under their INCI name:

Para-Aminobenzoic Acid Derivatives:
PABA,
Ethyl PABA,
Ethyl dihydroxypropyl PABA,
Ethylhexyl dimethyl PABA sold in particular under the name "Escalol 507" by ISP,
Glyceryl PABA,
PEG-25 PABA sold under the name "Uvinul P25" by BASF.

Salicylic Derivatives:
Homosalate sold under the name "Eusolex HMS" by Rona/EM Industries,
Ethylhexyl salicylate sold under the name "Neo Heliopan OS" by Haarmann and Reimer,
Dipropylene glycol salicylate sold under the name "Dipsal" by Scher,
TEA salicylate sold under the name "Neo Heliopan TS" by Haarmann and Reimer.

Dibenzoylmethane Derivatives:
Butyl methoxydibenzoylmethane sold in particular under the trademark "Parsol 1789" by Hoffmann LaRoche,
Isopropyldibenzoylmethane.

Cinnamnic Derivatives:
Ethylhexyl methoxycinnamate sold in particular under the trademark "Parsol MCX" by Hoffmann LaRoche,
Isopropyl methoxycinnamate,
Isoamyl methoxycinnamate sold under the trademark "Neo Heliopan E 1000" by Haarmann and Reimer,
Cinoxate,
DEA methoxycinnamate,
Diisopropyl methoxycinnamate,
Glyceryl ethylhexanoate dimethoxycinnamate.

β,β'-Diphenylacrylate Derivatives:
Octocrylene sold in particular under the trademark "Uvinul N539" by BASF,
Etocrylene sold in particular under the trademark "Uvinul N35" by BASF.

Benzophenone Derivatives:
Benzophenone-1 sold under the trademark "Uvinul 400" by BASF,
Benzophenone-2 sold under the trademark "Uvinul D50" by BASF,
Benzophenone-3 or Oxybenzone sold under the trademark "Uvinul M40" by BASF,
Benzophenone-4 sold under the trademark "Uvinul MS40" by BASF,
Benzophenone-5,
Benzophenone-6 sold under the trademark "Helisorb 11" by Norquay,
Benzophenone-8 sold under the trademark "Spectra-Sorb UV-24" by American Cyanamid,
Benzophenone-9 sold under the trademark "Uvinul DS-49" by BASF,
Benzophenone-12.

Benzylidenecamphor Derivatives:
3-Benzylidenecamphor manufactured under the name "Mexoryl SD" by Chimex,
4-Methylbenzylidenecamphor sold under the name "Eusolex 6300" by Merck,
Benzylidenecamphorsulfonic acid manufactured under the name "Mexoryl SL" by Chimex,
Camphor benzalkonium methosulfate manufactured under the name "Mexoryl SO" by Chimex,
Terephthalylidenedicamphorsulfonic acid manufactured under the name "Mexoryl SX" by Chimex,
Polyacrylamidomethylbenzylidenecamphor manufactured under the name "Mexoryl SW" by Chimex.

Phenylbenzimidazole Derivatives:
Phenylbenzimidazolesulfonic acid sold in particular under the trademark "Eusolex 232" by Merck,
Benzimidazilate, sold under the trademark "Neo Heliopan AP" by Haarmann and Reimer.

Triazine Derivatives:
Anisotriazine sold under the trademark "Tinosorb S" by Ciba Specialty Chemicals,
Ethylhexyltriazone sold in particular under the trademark "Uvinul T150" by BASF, Diethylhexylbutamidotriazone sold under the trademark "Uvasorb HEB" by Sigma 3V.

Phenylbenzotriazole Derivatives:

Drometrizole trisiloxane sold under the name "Silatrizole" by Rhodia Chimie.

Anthranilic Derivatives:

Menthyl anthranilate sold under the trademark "Neo Heliopan MA" by Haarmann and Reimer.

Imidazoline Derivatives:

Ethylhexyldimethoxybenzylidenedioxoimidazoline propionate.

Benzalmalonate Derivatives:

Polyorganosiloxane containing benzalmalonate functions, sold under the trademark "Parsol SLX" by Hoffmann LaRoche, and mixtures thereof.

The organic UV-screening agents that are more particularly preferred are chosen from the following compounds:
ethylhexyl salicylate,
butylmethoxydibenzoylmethane,
ethylhexyl methoxycinnamate,
octocrylene,
phenylbenzimidazolesulfonic acid,
terephthalylidenedicamphorsulfonic acid,
benzophenone-3,
benzophenone-4,
benzophenone-5,
4-methylbenzylidenecamphor,
benzimidazilate,
anisotriazine,
ethylhexyltriazone,
diethylhexylbutamidotriazone,
drometrizole trisiloxane, and mixtures thereof.

The additional soluble UV-screening agent(s) is(are) generally present in concentrations ranging from 0.1% to 15% by weight approximately and preferably from 0.2% to 10% by weight approximately relative to the total weight of the composition.

The compositions according to the invention may also contain agents for artificially tanning and/or browning the skin (self-tanning agents), for instance dihydroxyacetone (DHA).

The compositions of the invention may also comprise standard cosmetic adjuvants chosen especially from fatty substances, organic solvents, ionic or nonionic thickeners, softeners, antioxidants, free-radical scavengers, opacifiers, stabilizers, emollients, silicones, α-hydroxy acids, antifoams, moisturizers, vitamins, insect repellents, fragrances, preservatives, surfactants, fillers, photoprotective agents, polymers other than those of the invention, propellants, acidifying or basifying agents, colorants or any other ingredient usually used in cosmetics, in particular for the manufacture of antisun compositions in the form of emulsions.

The fatty substances may consist of an oil or a wax or mixtures thereof, and they also comprise fatty acids, fatty alcohols and fatty acid esters. The oils may be chosen from animal, plant, mineral and synthetic oils and especially from liquid petroleum jelly, liquid paraffin, volatile or nonvolatile silicone oils, isoparaffins, polyolefins, fluoro oils and perfluoro oils. Similarly, the waxes may be chosen from animal waxes, fossil waxes, plant waxes, mineral waxes and synthetic waxes that are known per se.

Among the organic solvents that may be mentioned are lower alcohols and polyols.

Needless to say, a person skilled in the art will take care to select this or these optional additional compound(s) and/or the amounts thereof such that the advantageous properties intrinsically linked to the compositions in accordance with the invention, and in particular the water resistance and the stability, are not, or not substantially, adversely affected by the envisaged addition(s).

The compositions of the invention may be prepared according to techniques that are well known to those skilled in the art, in particular those intended for preparing emulsions of oil-in-water or water-in-oil type.

These compositions may be in particular in the form of a simple or complex emulsion (O/W, W/O, O/W/O or W/O/W emulsion) such as a cream, a milk, a gel or a cream-gel, of a powder, of a solid tube, and may optionally be packaged as an aerosol and be in the form of a mousse or a spray.

When it is an emulsion, the aqueous phase of this emulsion may comprise a nonionic vesicular dispersion prepared according to known processes (Bangham, Standish and Watkins, *J. Mol. Biol.* 13, 238 (1965), FR-2,315,991 and FR-2,416,008).

The cosmetic composition of the invention may be used as a composition for protecting the human epidermis or the hair against ultraviolet rays, as an antisun composition or as a makeup product.

When the cosmetic composition according to the invention is used for protecting the human epidermis against UV rays, or as an antisun composition, it may be in the form of a suspension or a dispersion in solvents or fatty substances, in the form of a nonionic vesicular dispersion or in the form of an emulsion, preferably of oil-in-water type, such as a cream or a milk, or in the form of an ointment, a gel, a cream-gel, a solid tube, a powder, a stick, an aerosol mousse or a spray.

When the cosmetic composition according to the invention is used for protecting the hair against UV rays, it may be in the form of a shampoo, a lotion, a gel, an emulsion or a nonionic vesicular dispersion and may constitute, for example, a rinse-out composition, to be applied before or after shampooing, before or after dyeing or bleaching, before, during or after permanent-waving or straightening the hair, a styling or treating lotion or gel, a blow-drying or hairsetting lotion or gel, or a composition for permanent-waving, straightening, dyeing or bleaching the hair.

When the composition is used as a makeup product for the eyelashes, the eyebrows or the skin, such as an epidermal treatment cream, a foundation, a tube of lipstick, an eyeshadow, a face powder, a mascara or an eyeliner, it may be in solid or pasty, anhydrous or aqueous form, for instance oil-in-water or water-in-oil emulsions, nonionic vesicular dispersions or suspensions.

As a guide, for the antisun formulations in accordance with the invention, which contain a support of oil-in-water emulsion type, the aqueous phase (comprising especially hydrophilic screening agents) generally represents from 50% to 95% by weight and preferably from 70% to 90% by weight, relative to the total formulation, the oily phase (comprising especially lipophilic screening agents) represents from 5% to 50% by weight and preferably from 10% to 30% by weight, relative to the total formulation, and the (co)emulsifier(s) represent(s) from 0.5% to 20% by weight and preferably from 2% to 10% by weight, relative to the total formulation.

As mentioned at the start of the description, another subject of the present invention lies in the use of a composition according to the invention to manufacture cosmetic compositions for protecting the skin and/or the hair against ultraviolet radiation and in particular sunlight.

Another subject of the present invention lies in the use of an amphiphilic polymer as defined above to manufacture a photoprotective cosmetic or dermatological composition containing at least one organic UV-screening agent that is insoluble in the said emulsion, with the aim of increasing the water resistance of its screening power.

In order to further illustrate the present invention and the advantages thereof, the following specific examples are given, it being understood that same are intended only as illustrative and in nowise limitative. In said examples to follow, all parts and percentages are given by weight, unless otherwise indicated.

PREPARATION EXAMPLES

Preparation of the Ethoxylated (Meth)Acrylic Esters

These may be obtained especially by the action of glycidyl (meth)acrylate, or of (meth)acrylic acid, or of an alkyl (meth)acrylate, or of a (meth)acryloyl halide on an ethoxylated fatty alcohol. Non-limiting examples that may be mentioned include the following preparations:

a) using glycidyl methacrylate and Genapol T-250
b) using (meth)acrylic acid and Genapol UD-070
c) using methyl (meth)acrylate and Genapol LA-090
d) using (meth)acryloyl chloride and Genapol UD-070.

a) 500 g of Genapol T-250 and 75 g of glycidyl methacrylate are placed in a one-litre three-necked reactor equipped with a stirrer, a thermometer and a reflux condenser. The reaction mixture is heated at a temperature of 100° C. for 2 hours, and the excess glycidyl methacrylate is removed by distillation under reduced pressure. The monomer obtained may be used for the polymerization without further purification.

b) 500 g of Genapol UD-070, 100 g of (meth)acrylic acid and p-toluenesulfonic acid as catalyst are placed in a one-litre three-necked reactor equipped with a stirrer, a thermometer and a reflux condenser. The reaction mixture is refluxed for 2 hours, and the excess acid and water formed during the reaction are separated out by distillation under reduced pressure. The monomer obtained may be used for the polymerization without further purification.

c) 500 g of Genapol LA-090, 100 g of methyl (meth) acrylate and 20 g of titanium tetraisopropoxide are placed in a one-litre three-necked reactor equipped with a stirrer, a thermometer and a reflux condenser. The reaction mixture is refluxed for 2 hours and, after separation by distilling off the alcohol formed, the remaining ester is distilled under reduced pressure. The monomer obtained may be used for the polymerization without further purification.

d) 500 g of Genapol UD-070, 110 g of (meth)acryloyl chloride and 50 g of sodium carbonate are placed in a one-litre three-necked reactor equipped with a stirrer, a thermometer and a reflux condenser. The reaction mixture is refluxed for 2 hours, and the excess acid chloride is separated out by distillation under reduced pressure. The monomer obtained may be used for the polymerization without further purification.

Polymerization According to the Precipitation Method in Tert-Butanol 500 ml of tert-butanol and the calculated amount of AMPS are placed in a 2-litre reactor equipped with a reflux condenser, a gas inlet, a thermometer and a stirrer. The mixture is neutralized by introducing $NH_3$, and the monomer prepared above is added to the reaction mixture. The reaction mixture is made inert by passing nitrogen or argon through, and, when the internal temperature has reached 60° C., the initiator (AIBN) is introduced to initiate the polymerization.

After a few minutes, the polymer thus prepared precipitates. The mixture is refluxed for 2 hours and the polymer is separated from the solvent by vacuum filtration, and is then dried under reduced pressure.

The polymers below were prepared in the manner described above: (starting with the following reagents in amounts expressed in grams)

| | | | | |
|---|---|---|---|---|
| Genapol T-250 methacrylate | 10 | 20 | 30 | 97 |
| AMPS neutralized with $NH_3$ | 90 | 80 | 90 | 3 |
| Methylenebisacrylamide (crosslinking agent) | | | 1.5 | |
| Allyl methacrylate (crosslinking agent) | | 1.7 | | |
| TMPTA (crosslinking agent) | 1.8 | | | 1.8 |
| Azobisisobutyronitrile (initiator) | | | 1 | |
| 1 Dilauryl peroxide (initiator) | 1 | 1 | | 1 |
| tert-Butanol | 300 | 300 | 300 | 300 |

| Example 1 | grams |
|---|---|
| PHASE A: | |
| Octocrylene | 9 |
| (Uvinul N 539 from the company BASF) | |
| Butylmethoxydibenzoylmethane | 2.5 |
| (Parsol 1789 from the company Hoffmann LaRoche) | |
| Drometrizole trisiloxane | 0.75 |
| (Silatrizole from the company Rhodia) | |
| Decyl cocoate | 9 |
| (Tegosoft DC from the company Goldschmidt) | |
| PHASE B: | |
| 2-Acrylamido-2-methylpropansulfonic acid/n-dodecylacrylamide copolymer (3.5%/96.5% by weight) 100% neutralized with sodium hydroxide | 1.5 |
| PHASE C: | |
| Glycerol | 4 |
| Propylene glycol | 4 |
| Ethylenediaminetetraacetic acid, disodiium salt | 0.1 |
| Preservatives | qs |
| Terephthalylidenedicamphorsulfonic acid | 1.5 |
| (Mexoryl SX from the company Chimex) | |
| Triethanolamine | 0.26 |
| Water | qs 100 g |
| PHASE D: | |
| Anatase titanium oxide (60 nm) coated with silica/alumina, as a protected aqueous dispersion | 16.7 |

Procedure

Phases A and B are mixed together and heated to 70° C. Phase C is mixed with the mixture obtained (A+B) with stirring using a Moritz blender, and the mixture is left to cool. Phase D is then added.

Example 2

Similar results were obtained by replacing the 2-acrylamido-2-methylpropanesulfonic acid/n-dodecylacrylamide copolymer neutralized with sodium hydroxide, of the above example, with a copolymer crosslinked with methylenebisacrylamide consisting of 75% by weight of AMPS units neutralized with $NH_3$ and 25% by weight of units of formula (III) in which $R_1$=H, $R_4$=$C_{16}$–$C_{18}$ and x=25.

Example 3

Similar results were obtained by replacing the 2-acrylamido-2-methylpropanesulfonic acid/n-dodecylacrylamide copolymer neutralized with sodium hydroxide, of the above example, with a copolymer crosslinked with allyl methacrylate consisting of 90% by weight of AMPS units neutralized with NH$_3$ and 10% by weight of Genapol T-250 methacrylate units [units of formula (III) in which R$_1$=CH$_3$, R$_4$=C$_{16}$–C$_{18}$ and x=25], or with a copolymer crosslinked with allyl methacrylate consisting of 80% by weight of AMPS units neutralized with NH$_3$ and 20% by weight of Genapol T-250 methacrylate units [units of formula (III) in which R$_1$=CH$_3$, R$_4$=C$_{16}$–C$_{18}$ and x=25].

Each patent, patent application, publication and literature article/report cited or indicated herein is hereby expressly incorporated by reference.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A photoprotective cosmetic/dermatological composition suited for the UV-photoprotection of the skin and/or hair, comprising (a) particulates of at least one insoluble mineral and/or organic UV-screening agent having a particle size ranging from 5 nm to 5 μm and (b) a stabilizing amount of at least one amphiphilic polymerizate of at least one ethylenically unsaturated monomer which comprises a sulfonic group, whether in the free acid or in partially or totally neutralized state, and which amphiphilic polymerizate also comprises at least one hydrophobic moiety.

2. The cosmetic/dermatological composition as defined by claim 1, said at least one hydrophobic moiety of said at least one amphiphilic polymerizate having from 6 to 50 carbon atoms.

3. The cosmetic/dermatological composition as defined by claim 2, said at least one hydrophobic moiety of said at least one amphiphilic polymerizate having from 6 to 22 carbon atoms.

4. The cosmetic/dermatological composition as defined by claim 3, said at least one hydrophobic moiety of said at least one amphiphilic polymerizate having from 6 to 18 carbon atoms.

5. The cosmetic/dermatological composition as defined by claim 4, said at least one hydrophobic moiety of said at least one amphiphilic polymerizate having from 12 to 18 carbon atoms.

6. The cosmetic/dermatological composition as defined by claim 1, the sulfonic groups of said at least one amphiphilic polymerizate being partially or totally neutralized with a mineral or organic base.

7. The cosmetic/dermatological composition as defined by claim 1, said at least one amphiphilic polymerizate having a number-average molecular weight ranging from 1,000 to 20,000,000 g/mol.

8. The cosmetic/dermatological composition as defined by claim 7, said number-average molecular weight ranging from 20,000 to 5,000,000 g/mol.

9. The cosmetic/dermatological composition as defined by claim 8, said number-average molecular weight ranging from 100,000 to 1,500,000 g/mol.

10. The cosmetic/dermatological composition as defined by claim 1, an aqueous 1% by weight solution of said at least one amphiphic polymerizate having, at a temperature of 25° C., a viscosity, measured using a Brookfield viscometer with a No. 7 needle, ranging from 20,000 mPa.s to 100,000 mPa.s.

11. The cosmetic/dermatological composition as defined by claim 1, said at least one amphiphilic polymerizate having been prepared by free-radical precipitation polymerization in tert-butanol.

12. The cosmetic/dermatological composition as defined by claim 1, said at least one amphiphilic polymerizate being non-crosslinked.

13. The cosmetic/dermatological composition as defined by claim 1, said at least one amphiphilic polymerizate being crosslinked.

14. The cosmetic/dermatological composition as defined by claim 13, said at least one amphiphilic polymerizate being crosslinked with a polyolefinically unsaturated crosslinking agent.

15. The cosmetic/dermatological composition as defined by claim 14, said crosslinking agent comprising methylenebisacrylamide, allyl methacrylate or trimethylolpropane triacrylate (TMPTA).

16. The cosmetic/dermatological composition as defined by claim 14, the degree of crosslinking ranging from 0.01 mol % to 10 mol %.

17. The cosmetic/dermatological composition as defined by claim 1, said at least one ethylenically unsaturated monomer which comprises a sulfonic group comprising vinylsulfonic acid, styrenesulfonic acid, a (meth)acrylamido (C$_1$–C$_{22}$)alkylsulfonic acid, an N—(C$_1$–C$_{22}$)alkyl(meth) acrylamido-(C$_1$–C$_{22}$)alkylsulfonic acid, or the partially or totally neutralized forms thereof.

18. The cosmetic/dermatological composition as defined by claim 17, said at least one ethylenically unsaturated monomer which comprises a sulfonic group comprising acrylamidomethanesulfonic acid, acrylamidoethanesulfonic acid, acrylamidopropanesulfonic acid, 2-acrylamido-2-methylpropanesulfonic acid, methacrylamido-2-methylpropanesulfonic acid, 2-acrylamido-n-butanesulfonic acid, 2-acrylamido-2,4,4-trimethylpentanesulfonic acid, 2-methacryl-amidododecylsulfonic acid or 2-acrylamido-2, 6-di-methyl-3-heptanesulfonic acid, or the partially or totally neutralized forms thereof.

19. The cosmetic/dermatological composition as defined by claim 18, said at least one ethylenically unsaturated monomer which comprises a sulfonic group comprising 2-acrylamido-2-methylpropanesulfonic acid (AMPS), or the partially or totally neutralized forms thereof.

20. The cosmetic/dermatological composition as defined by claim 19, said at least one amphiphilic polymerizate comprising a random AMPS polymer modified by reaction with an n-mono(C$_6$–C$_{22}$)alkylamine or a di-n-(C$_6$–C$_{22}$)-alkylamine.

21. The cosmetic/dermatological composition as defined by claim 19, said amphiphilic AMPS polymerizate also being derived from at least one ethylenically unsaturated monomer not comprising a fatty chain.

22. The cosmetic/dermatological composition as defined by claim 20, said at least one ethylenically unsaturated monomer not comprising a fatty chain being selected from among (meth)acrylic acids and the β-substituted alkyl derivatives thereof, and the esters thereof obtained with monoalcohols or mono- or polyalkylene glycols, or from (meth)acrylamides, vinylpyrrolidone, maleic anhydride, itaconic acid or maleic acid, or mixtures thereof.

23. The cosmetic/dermatological composition as defined by claim 19, said amphiphilic AMPS polymerizate comprising an amphiphilic copolymer of AMPS and of at least one ethylenically unsaturated hydrophobic monomer which comprises at least one hydrophobic moiety having from 6 to 50 carbon atoms.

24. The cosmetic/dermatological composition as defined by claim 23, said at least one hydrophobic moiety having from 6 to 22 carbon atoms.

25. The cosmetic/dermatological composition as defined by claim 24, said at least one hydrophobic moiety having from 6 to 18 carbon atoms.

26. The cosmetic/dermatological composition as defined by claim 25, said at least one hydrophobic moiety having from 12 to 18 carbon atoms.

27. The cosmetic/dermatological composition as defined by claim 23, said at least one ethylenically unsaturated hydrophobic monomer comprising an acrylate or acrylamide of formula (I) below:

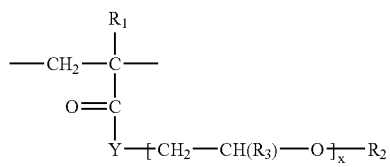

(I)

in which $R_1$ and $R_3$, which may be identical or different, are each a hydrogen atom or a linear or branched $C_1$–$C_6$ alkyl radical; Y is O or NH; $R_2$ is a hydrophobic hydrocarbyl radical having from 6 to 50 carbon atoms; and $\underline{x}$ is the number of moles of alkylene oxide and ranges from 0 to 100.

28. The cosmetic/dermatological composition as defined by claim 27, wherein formula (I) said hydrophobic radical $R_2$ is a linear, branched or cyclic $C_6$–$C_{18}$ alkyl radical; $C_6$–$C_{18}$ alkylperfluoro radical; cholesteryl radical or a cholesterol ester; or an aromatic polycyclic radical.

29. The cosmetic/dermatological composition as defined by claim 27, said at least one monomer of formula (I) comprising at least one alkylene oxide structural unit ($x \geq 1$).

30. The cosmetic/dermatological composition as defined by claim 27, said at least one monomer of formula (I) comprising at least one polyoxyalkylenated structural unit.

31. The cosmetic/dermatological composition as defined by claim 30, said at least one polyoxyalkylenated structural unit comprising ethylene oxide groups and/or of propylene oxide groups.

32. The cosmetic/dermatological composition as defined by claim 31, said at least one polyoxyalkylenated structural unit solely comprising ethylene oxide groups.

33. The cosmetic/dermatological composition as defined by claim 27, wherein formula (I) the number of oxyalkylenated structural units ranges from 3 to 100.

34. The cosmetic/dermatological composition as defined by claim 33, wherein formula (I) the number of oxyalkylenated structural units ranges from 3 to 50.

35. The cosmetic/dermatological composition as defined by claim 34, wherein formula (I) the number of oxyalkylenated structural units ranges from 7 to 25.

36. The cosmetic/dermatological composition as defined by claim 23, said at least one amphiphilic AMPS polymer comprising a crosslinked or non-crosslinked, neutralized or non-neutralized copolymer which comprises from 15% to 60% by weight of AMPS structural units and from 40% to 85% by weight of ($C_8$–$C_{16}$)alkyl(meth)acrylamide structural units or of ($C_8$–$C_{16}$)alkyl (meth)acrylate structural units, relative to the polymer; or a terpolymer which comprises from 10 mol % to 90 mol % of acrylamide structural units, from 0.1 mol % to 10 mol % of AMPS structural units and from 5 mol % to 80 mol % of n-($C_6$–$C_{18}$)alkyl-acrylamide structural units, relative to the polymer.

37. The cosmetic/dermatological composition as defined by claim 23, said at least one amphiphilic AMPS polymer comprising a non-crosslinked copolymer of partially or totally neutralized AMPS and of n-dodecyl methacrylate, or a crosslinked or non-crosslinked copolymer of partially or totally neutralized AMPS and of n-dodecyl-methacrylamide.

38. The cosmetic/dermatological composition as defined by claim 23, said at least one amphiphilic AMPS polymer comprising a copolymer of 2-acrylamido-2-methylpropanesulfonic acid (AMPS) structural units of formula (II) below:

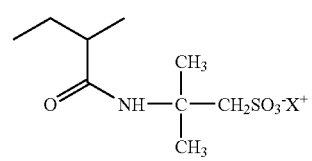

(II)

in which $X^+$ is a proton, an alkali metal cation, an alkaline earth metal cation or the ammonium ion, and of structural units of formula (III) below:

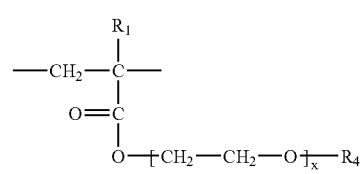

(III)

in which $\underline{x}$ is an integer ranging from 3 to 100, $R_1$ is as defined in formula (I); and $R_4$ is a linear or branched $C_6$–$C_{22}$ alkyl radical.

39. The cosmetic/dermatological composition as defined by claim 38, wherein formula (III) $\underline{x}$=25, $R_1$ is methyl and $R_4$ is n-dodecyl.

40. The cosmetic/dermatological composition as defined by claim 38, the molar percentage of structural units of formula (I) or of structural units of formula (III) in the polymer ranging from 50.1% to 99.9%.

41. The cosmetic/dermatological composition as defined by claim 38, the molar percentage of structural units of formula (I) or of structural units of formula (III) in the polymer ranging from 0.1% to 50%.

42. The cosmetic/dermatological composition as defined by claim 1, said at least one amphiphilic polymerizate comprising from 0.01% to 30% by weight thereof.

43. The cosmetic/dermatological composition as defined by claim 1, comprising at least one insoluble organic UV-screening selected from among oxanilide, triazine, triazole, vinyl amide, cinnamide or benzazole organic UV-screening agents.

44. The cosmetic/dermatological composition as defined by claim 43, comprising at least one oxanilide UV-screening agent of formula (1):

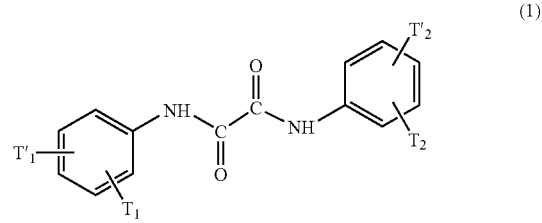

(1)

in which $T_1$, $T'_1$, $T_2$ and $T'_2$, which may be identical or different, are each a $C_1$–$C_8$ alkyl radical or a $C_1$–$C_8$ alkoxy radical.

45. The cosmetic/dermatological composition as defined by claim 44, said at least one oxanilide UV-screening agent being selected from the following compounds:

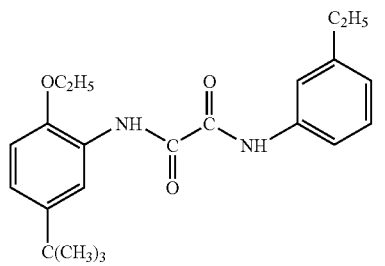

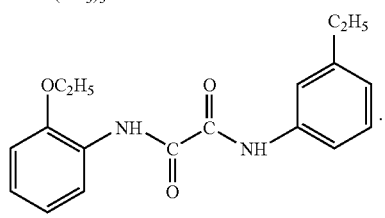

46. The cosmetic/dermatological composition as defined by claim 43, comprising at least one triazine UV-screening agent selected from among insoluble s-triazine compounds bearing benzalmalonate and/or phenylcyanoacylate substituents.

47. The cosmetic/dermatological composition as defined by claim 46, said at least one triazine UV-screening agent being selected from among the following compounds:
- 2,4,6-tris(diethyl 4'-aminobenzalmalonate)-s-triazine,
- 2,4,6-tris(diisopropyl 4'-aminobenzalmalonate)-s-triazine,
- 2,4,6-tris(dimethyl 4'-aminobenzalmalonate)-s-triazine, and
- 2,4,6-tris(ethyl α-cyano-4-aminocinnamate)-s-triazine.

48. The cosmetic/dermatological composition as defined by claim 43, said at least one triazine UV-screening agent having the formula (2):

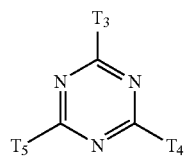

(2)

in which $T_3$, $T_4$ and $T_5$, which may be identical or different, are each phenyl, phenoxy or pyrrolo, optionally substituted with one, two or three substituents selected from among OH, $C_1$–$C_{18}$ alkyl or alkoxy, $C_1$–$C_{18}$ carboxyalkyl, $C_5$–$C_8$ cycloalkyl, a methylidenecamphor group or a group —(CH=CH)$_n$(CO)—OT$_6$, with $T_6$ being either $C_1$–$C_{18}$ alkyl or cinnamyl, and n is 0 or 1.

49. The cosmetic/dermatological composition as defined by claim 43, said at least one triazine UV-screening agent comprising an insoluble s-triazine compound bearing benzotriazole and/or benzothiazole substituents.

50. The cosmetic/dermatological composition as defined by claim 49, said at least one triazine UV-screening agent being selected from:
- 2,4,6-tris[(3'-benzotriazol-2-yl-2'-hydroxy-5'-methyl)phenylamino]-s-triazine, and
- 2,4,6-tris[(3'-benzotriazol-2-yl-2'-hydroxy-5'-tert-octyl)phenylamino]-s-triazine.

51. The cosmetic/dermatological composition as defined by claim 43, comprising at least one triazole UV-screening agent having the formula (3) below:

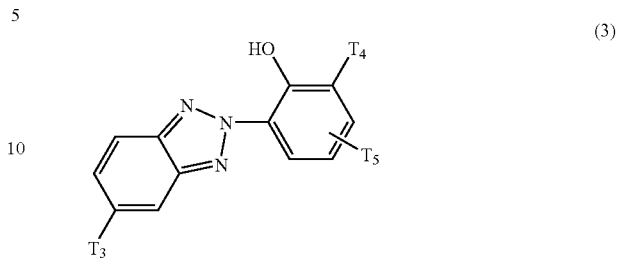

(3)

in which $T_3$ is a hydrogen atom or a $C_1$–$C_{18}$ alkyl radical; and $T_4$ and $T_5$, which may be identical or different, are each a $C_1$–$C_{18}$ alkyl radical optionally substituted with a phenyl group.

52. The cosmetic/dermatological composition as defined by claim 51, said at least one compound of formula (3) being selected from among the following compounds

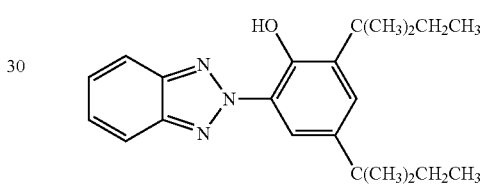

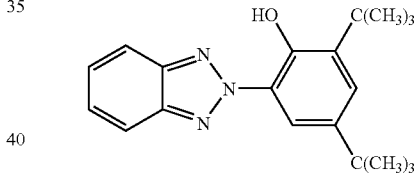

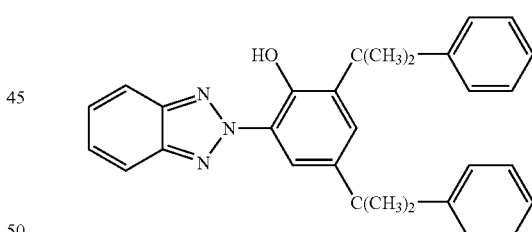

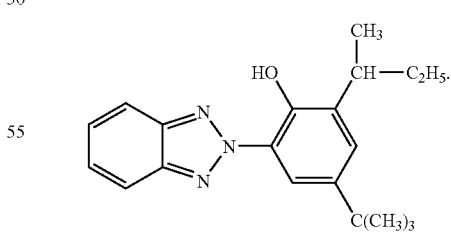

53. The cosmetic/dermatological composition as defined by claim 43, said at least one insoluble UV-screening agent comprising [2,4'-dihydroxy-3-(2H-benzotriazol-2-yl)-5-(1,1,3,3-tetramethylbutyl)-2'-n-octoxy-5'-benzoyl]-diphenylmethane having the structure:

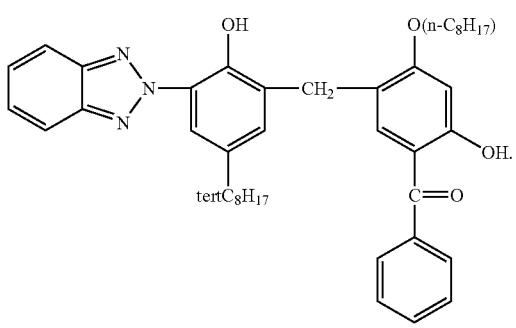

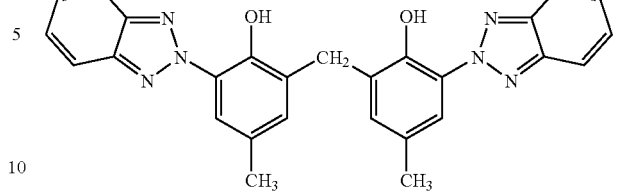

54. The cosmetic/dermatological composition as defined by claim 43, comprising at least one triazole UV-screening agent selected from among the methylenebis(hydroxyphenyl-benzotriazole) compounds of the following formula (4):

(4)

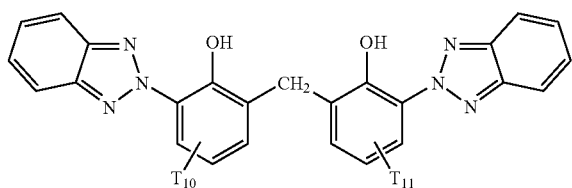

in which the radicals $T_{10}$ and $T_{11}$, which may be identical or different, are each a $C_1$–$C_{18}$ alkyl radical that may be substituted with one or more radicals selected from among $C_1$–$C_4$ alkyl radicals, $C_5$–$C_{12}$ cycloalkyl radicals and aryl radicals.

55. The cosmetic/dermatological composition as defined by claim 54, said at least one compound of formula (4) being selected from among those having the following structures:

compound (a)

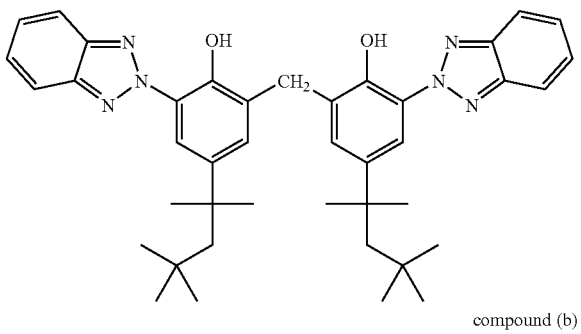

compound (b)

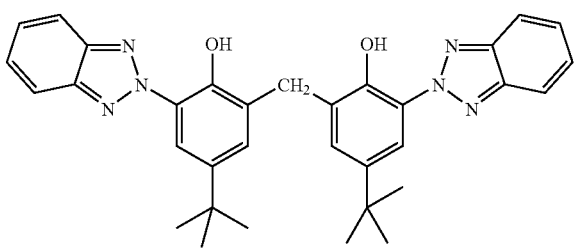

compound (c)

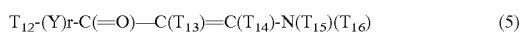

56. The cosmetic/dermatological composition as defined by claim 43, comprising at least one vinyl amide UV-screening agent having the following formula (5):

$$T_{12}\text{-}(Y)r\text{-}C(=O)\text{---}C(T_{13})=C(T_{14})\text{-}N(T_{15})(T_{16}) \quad (5)$$

in which $T_{12}$ is a $C_1$–$C_{18}$ alkyl radical or a phenyl group optionally substituted with one, two or three radicals selected from among OH, $C_1$–$C_{18}$ alkyl and $C_1$–$C_8$ alkoxy, or a group —C(=O)—O$T_{17}$ in which $T_{17}$ is a $C_1$–$C_{18}$ alkyl radical; $T_{13}$, $T_{14}$, $T_{15}$ and $T_{16}$, which may be identical or different, are each a $C_1$–$C_{18}$ alkyl radical or a hydrogen atom; Y is N or O and r is 0 or 1.

57. The cosmetic/dermatological composition as defined by claim 56, said at least one compound of formula (5) being selected from among:

4-octylamino-3-penten-2-one;

ethyl 3-octylamino-2-butenoate;

3-octylamino-1-phenyl-2-buten-1-one, and 3-dodecylamino-1-phenyl-2-buten-1-one.

58. The cosmetic/dermatological composition as defined by claim 43, comprising at least one cinnamamide UV-screening agent having the following formula (6):

(6)

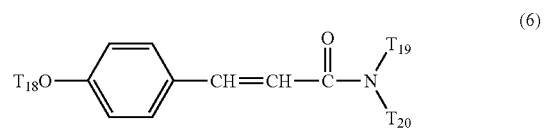

in which O$T_{18}$ is a hydroxyl or $C_1$–$C_4$ alkoxy radical; $T_{19}$ is hydrogen or a $C_1$–$C_4$ radical; $T_{20}$ is a group —(CONH)s-phenyl in which s is 0 or 1 and the phenyl group may be substituted with one, two or three groups selected from among OH, $C_1$–$C_{18}$ alkyl and $C_1$–$C_8$ alkoxy, or a group —C(=O)—O$T_{21}$ in which $T_{21}$ is a $C_1$–$C_{18}$ alkyl radical.

59. The cosmetic/dermatological composition as defined by claim 43, comprising at least one cinnamamide dimer UV-screening agent.

60. The cosmetic/dermatological composition as defined by claim 59, said at least one insoluble UV-screening agent comprising the compound having the structural formula:

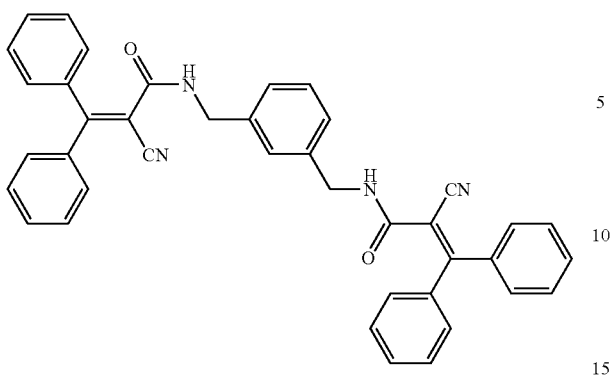

61. The cosmetic/dermatological composition as defined by claim 43, comprising at least one insoluble benzazole UV-screening agent selected from among those corresponding to one of the formulae (7), (8) and (9) below:

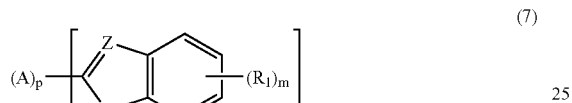

(7)

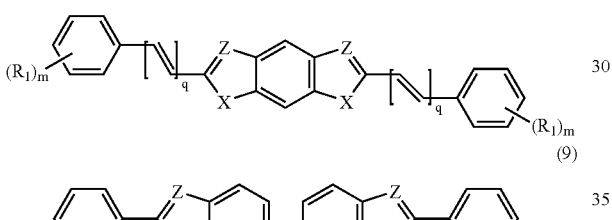

(8)

(9)

in which each of the symbols X independently represents an oxygen or sulfur atom or a group $NR_2$, each of the symbols Z independently represents a nitrogen atom or a CH group, each of the symbols $R_1$ independently represents an OH group, a halogen atom, a linear or branched $C_1$–$C_8$ alkyl radical optionally containing a silicon atom, or a linear or branched $C_1$–$C_8$ alkoxy radical, each of the numbers m is independently 0, 1 or 2, n represents an integer ranging from 1 to 4 inclusive, p is equal to 0 or 1, each of the numbers q is independently equal to 0 or 1, each of the symbols $R_2$ independently represents a hydrogen atom or a linear or branched $C_1$–$C_8$ alkyl radical or benzyl group optionally containing a silicon atom;

A represents a radical of valency n selected from among those of formulae:

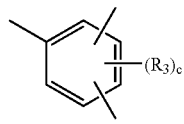 (a)

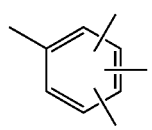 (b)

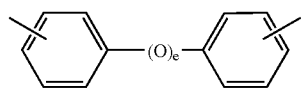 (c)

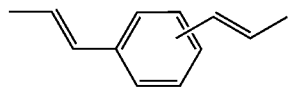 (d)

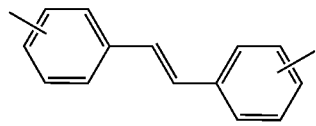 (e)

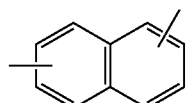 (f)

 (g)

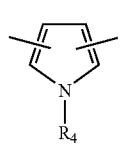 (h)

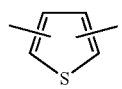 (i)

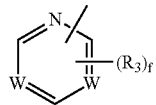 (j)

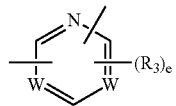 (k)

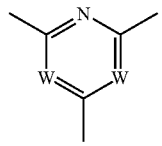 (l)

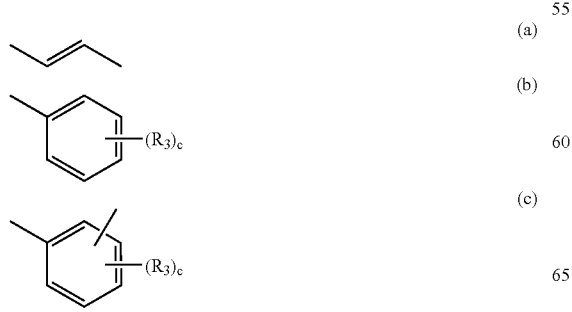

(m)

(n)

(o)

in which each of the symbols $R_3$ independently represents a halogen atom or a linear or branched $C_1$–$C_4$ alkyl or alkoxy radical, or hydroxyl; $R_4$ represents a hydrogen atom or a linear or branched $C_1$–$C_4$ alkyl radical; c=0–4; d=0–3; e=0 or 1 and f=0–2.

62. The cosmetic/dermatological composition as defined by claim 61, in which the at least one benzazole compound of formula (7) is selected from among 2-benzoxazole-2-yl- 4-methylphenol, 2-(1H-benzimidazol-2-yl)-4-methoxyphenol or 2-benzothiazol-2-ylphenol, 2,2'-bis(benzimidazole), 5,5',6,6'-tetramethyl-2,2'-bis(benzimidazole), 5,5'-dimethyl-2,2'-bis(benzimidazole), 6-methoxy-2,2'-bis(benzimidazole), 2-(1H-benzimidazol-2-yl)benzothiazole, 2-(1H-benzimidazol-2-yl)benzoxazole and N,N'-dimethyl-2,2'-bis(benzimidazole), 1,4-phenylenebis(2-benzoxazolyl), 1,4-phenylenebis(2-benzimidazolyl), 1,3-phenylenebis(2-benzoxazolyl), 1,2-phenylenebis(2-benzoxazolyl), 1,2-phenylenebis) benzimidazolyl), 1,4-phenylenebis(N-2-ethylhexyl-2-benzimidazolyl) and 1,4-phenylenebis(N-trimethylsilylmethyl-2-benzimidazolyl), 2-(2-benzofuryl)-benzoxazole, 2-(benzofuryl)-5-methylbenzoxazole and 2-(3-methyl-2-benzofuryl)benzoxazole.

63. The cosmetic/dermatological composition as defined by claim 61, in which the at least one benzazole compound of formula (8) is selected from among 2,6-diphenyl-1,7-dihydrobenzo[1,2-d;4,5-d']di-imidazole, 2,6-distyryl-1,7-dihydrobenzo[1,2-d;4,5-d']diimidazole and 2,6-di(p-tert-butylstyryl)-1,7-dihydrobenzo[1,2-d;4,5-d']diimidazole.

64. The cosmetic/dermatological composition as defined by claim 61, in which the at least one benzazole compound of formula (9) comprises 5,5'-bis[(2-phenyl)benzimidazole].

65. The cosmetic/dermatological composition as defined by claim 61, in which the at least one insoluble benzazole UV-screening agent comprises 2-(1H-benzimidazol-2-yl)benzoxazole, 6-methoxy-2,2'-bis-(benzimidazole), 2-(1H-benzimidazole-2-yl)benzothiazole, 1,4-phenylenebis(2-benzoxazolyl), 1,4-phenylenebis(2-benzimidazolyl), 1,3-phenylenebis(2-benzoxazolyl), 1,2-phenylenebis(2-benzoxazolyl), 1,2-phenylenebis(2-benzimidazolyl) or 1,4-phenylene-bis(N-trimethylsilylmethyl-2-benzimidazolyl).

66. The cosmetic/dermatological composition as defined by claim 1, said at least one insoluble UV-screening agent comprising a multivalent metal salt of a sulfonic or carboxylic organic UV-screening agent.

67. The cosmetic/dermatological composition as defined by claim 66, said at least one insoluble UV-screening agent comprising a multivalent metal salt of a sulfonated benzylidene-camphor compound; a multivalent metal salt of a sulfonated benzimidazole compound; a multivalent metal salt of a cinnamic acid compound.

68. The cosmetic/dermatological composition as defined by claim 1, said at least one insoluble UV-screening agent comprising a complex of a multivalent metal or of ammonium or of substituted ammonium of a UV-A and/or UV-B organic screening agent.

69. The cosmetic/dermatological composition as defined by claim 1, said at least one insoluble UV-screening agent comprising from 0.1% to 25% by weight thereof.

70. The cosmetic/dermatological composition as defined by claim 1, further comprising at least one active agent for artificially tanning and/or browning the skin.

71. The cosmetic/dermatological composition as defined by claim 1, further comprising at least one UV-A-active and/or UV-B-active soluble organic UV-screening agent.

72. The cosmetic/dermatological composition as defined by claim 71, said at least one soluble organic UV-screening agent being selected from among anthranilates; cinnamic derivatives; dibenzoylmethane derivatives; salicylic derivatives; camphor derivatives; triazine derivatives; benzophenone derivatives; β,β'-diphenylacrylate derivatives; benzotriazole derivatives; benzalmalonate derivatives; benzimidazole derivatives; imidazolines; bis-benzazolyl derivatives; p-aminobenzoic acid (PABA) derivatives; screening polymers and screening silicones; dimers derived from α-alkylstyrene; 4,4-di-arylbutadienes, and mixtures thereof.

73. The cosmetic/dermatological composition as defined by claim 72, said at least one soluble organic UV-screening agent being selected from among:

ethylhexyl salicylate, butylmethoxydibenzoylmethane, ethylhexyl methoxycinnamate, octocrylene, phenylbenzimidazolesulfonic acid, terephthalylidenedicamphorsulfonic acid, benzophenone-3, benzophenone-4, benzophenone-5, 4-methylbenzylidenecamphor, benzimidazilate, anisotriazine, ethylhexyltriazone, diethylhexylbutamidotriazone, drometrizole trisiloxane, and mixtures thereof.

74. The cosmetic/dermatological composition as defined by claim 1, further comprising at least one adjuvant selected from among fatty substances, organic solvents, ionic or nonionic thickeners, softeners, antioxidants, free-radical scavengers, opacifiers, stabilizers, emollients, silicones, a-hydroxy acids, antifoams, moisturizers, vitamins, insect repellents, fragrances, preservatives, surfactants, fillers, photoprotective agents, polymers other than those of the invention, propellants, acidifying or basifying agents and colorants.

75. The cosmetic/dermatological composition as defined by claim 1, formulated as a nonionic vesicular dispersion, an emulsion, a cream a milk, a gel, a cream-gel, a suspension, a dispersion, a powder, a solid tube, a mousse or spray.

76. The cosmetic/dermatological composition as defined by claim 1, formulated as a makeup composition for the eyelashes, the eyebrows or the skin, in solid or pasty, anhydrous or aqueous form, or in the form of an emulsion, a suspension or a dispersion.

77. The cosmetic/dermatological composition as defined by claim 1, formulated as a composition for protecting the hair against ultraviolet rays and in the form of a shampoo, a lotion, a gel, an emulsion or a nonionic vesicular dispersion.

78. A regime or regimen for photoprotecting the skin and/or hair against the damaging effects of UV-irradiation, comprising topically applying thereon a thus effective amount of a photoprotective cosmetic/dermatological composition, comprising (a) particulates of at least one insoluble mineral and/or organic UV-screening agent having a particle size ranging from 5 nm to 5 µm and (b) a stabilizing amount of at least one amphiphilic polymerizate of at least one ehtylenically unsaturated monomer which comprises a sulfonic group, whether in the free acid or in partially or totally neutralized state, and which amphiphilic polymerizate also comprises at least one hydrophobic moiety.

* * * * *